United States Patent [19]

Kaan et al.

[11] Patent Number: 5,712,283

[45] Date of Patent: Jan. 27, 1998

[54] METHOD OF INHIBITING HYPERGLYCEMIA AND PHARMACEUTICAL COMPOSITION FOR USE THEREIN

[75] Inventors: Elbert Kaan, Grossburgwedel; Dieter Ziegler, Hemmingen; Reinhard Brueckner, Hanover, all of Germany

[73] Assignee: Kali-Chemie Pharma GmbH, Hanover, Germany

[21] Appl. No.: 492,656

[22] Filed: Jun. 20, 1995

[30] Foreign Application Priority Data

Jul. 1, 1994 [DE] Germany .......................... 44 23 177.6

[51] Int. Cl.⁶ .................................................. A01N 43/50
[52] U.S. Cl. ................................................. 514/269
[58] Field of Search ........................................ 514/269

[56] References Cited

U.S. PATENT DOCUMENTS

| | | |
|---|---|---|
| 4,323,570 | 4/1982 | Stenzel et al. . |
| 5,296,498 | 3/1994 | Malen et al. . |
| 5,494,934 | 2/1996 | Malen et al. . |

OTHER PUBLICATIONS

Mueller et al., "Steady State Investigation of Possible Pharmokinetic Interactions of Moxonidine and Glibenclamide" European Journal of Drug Metabolism and Pharmokinetics, 1993, vol. 18, No. 3, pp. 277–283.

Abstract of Published German Patent Application No. DE 2,849,537, Mar. 17, 1983 Derwent.

Schwarz et al., "Langzeiterfahrungen mit Moxonidin, einem neuen Antihypertensivum" (Long–Term Experience with Moxonidine, a new Anti–hypertensive Drug), *Fortschr. Med.*, 108:(32) 616–20 (1990).

Trieb et al., "Wirksamkeit und Vertraeglichkeit des Imidazol–Rezeptor–Agonisten" (Effectiveness and Compatibility of the Imidazole Receptor Against), *Medwelt*, 45:440–45 (1994).

Rupp et al., "Modification of Myosin Isozymes and SR Ca²⁺pump ATPase of the Diabetic Rat . . . ", *Molecular and Cellular Biology*, 132:69–80 (1994).

Michel et al., "From α₂–Adrenoceptors to Imidazoline Receptors: Putative Progress for Cardiovasular Therapy", *Journal of Cardiovascular Pharmacology*, 20 (Suppl. 4):S24–S30 (1992).

Rupp et al., *Therapiewoche*, vol. 43, Nos. 32/33, pp. 1686–1693 (1993).

Dotzer et al., *Z. Allg. Med.*, 68:760–763 (1992).

*Primary Examiner*—Jeffrey C. Mullis
*Attorney, Agent, or Firm*—Evenson, McKeown, Edwards & Lenahan P.L.L.C.

[57] ABSTRACT

A method of using moxonidine or a physiologically acceptable acid addition salt thereof for the treatment and/or prophylaxis of hyperglycaemia, and pharmaceutical compositions for use therein.

12 Claims, No Drawings

METHOD OF INHIBITING HYPERGLYCEMIA AND PHARMACEUTICAL COMPOSITION FOR USE THEREIN

BACKGROUND OF THE INVENTION

The present invention relates to the use of 4-chloro-5-[(4,5-dihydro-1H-imidazol-2-yl)amino]-6-methoxy-2-methylpyrimidine (=moxonidine) and its physiologically acceptable acid addition salts for the treatment and/or prophylaxis of hyperglycaemias, and for the production of medicaments suitable for this treatment.

SUMMARY OF THE INVENTION

It is the object of the invention to provide a method of inhibiting hyperglycemia.

Another object is to provide novel pharmaceutical preparations for the treatment of metabolic disorders which can lead to hyperglycaemias.

In accordance with a first aspect of the invention, the object is achieved by providing a method of inhibiting hyperglycemia in a mammal by administering to said mammal an effective hyperglycemia inhibiting amount of a compound corresponding to formula I

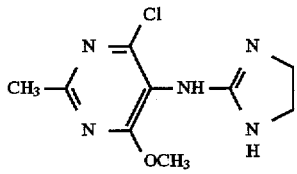

or a physiologically acceptable acid addition salt thereof.

In accordance with a further aspect of the invention, 4-chloro-5-[(4,5-dihydro-1H-imidazol-2-yl)amino]-6-methoxy-2-methylpyrimidine of formula I

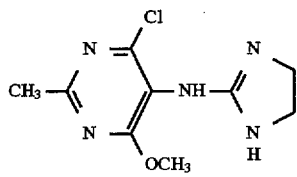

and its physiologically acceptable acid addition salts are used for the production of pharmaceutical preparations for the treatment of hyperglycaemias.

Suitable physiologically acceptable acid addition salts of moxonidine include salts with inorganic acids, for example hydrohalic acids, or with organic acids, for example lower aliphatic monocarboxylic or dicarboxylic acids such as acetic acid, fumaric acid or tartaric acid or aromatic carboxylic acids such as e.g. salicylic acid.

The compounds employed according to the invention for the treatment of hyperglycaemic conditions fall under the scope of 5-[(2-imidazolin-2-yl)amino]pyrimidine derivatives having hypotensive properties described in German Offenlegungsschrift No. 28 49 537, and are disclosed in this Patent Application. Moxonidine-containing pharmaceutical preparations are obtainable commercially as antihypertensives under the trade name Physiotens™ and are employed medicinally as an antihypertensive. The compounds can be prepared in a known manner in accordance with, or analogously to, the process described in the aforementioned German Offenlegungsschrift.

DETAILED DESCRIPTION OF PREFERRED EMBODIMENTS

It has now surprisingly been found that moxonidine and its physiologically acceptable acid addition salts have an antihyperglycaemic action in humans and larger mammals and are suitable for the treatment of disorders of the glucose metabolism of varying origin which are associated with hyperglycaemia, for example the occurrence of raised plasma glucose values as a result of increased glucose release and/or decreased metabolic glucose utilization, which can be connected with raised blood pressure, insulin resistance, glucose intolerance, type II diabetes and/or obesity.

For the treatment according to the invention of hyperglycaemic conditions, moxonidine and its physiologically acceptable acid addition salts can be administered orally, intravenously or even transdermally in customary pharmaceutical preparations.

Antihyperglycaemically active amounts of the compounds according to the invention can thus be contained in solid or liquid pharmaceutical preparations together with customary pharmaceutical auxiliaries and/or excipients. Examples of solid preparations which may be mentioned include orally adminstrable preparations such as tablets, coated tablets, capsules, powders or granules or even suppositories. These solid preparations can contain conventional inorganic and/or organic pharmaceutical excipients such as e.g. lactose, talc or starch in addition to conventional pharmaceutical adjuvants, for example lubricants or tablet disintegrants. Liquid preparations such as solutions, suspensions or emulsions of the active compounds may contain the customary diluents such as water, oils and/or suspending agents such as polyethylene glycols and the like. Further adjuvants can additionally be added, such as e.g. preservatives, flavor correctants and the like.

The active compounds can be mixed and formulated with the pharmaceutical adjuvants and/or excipients in a known manner. In order to prepare solid pharmaceutical forms, for example, the active compounds can be mixed and granulated in wet or dry form with the adjuvants and/or excipients in a customary manner. The granules or powder can then be filled directly into capsules or compressed to give tablet cores in a conventional manner. If desired, these can be sugar coated in a known manner.

The antihyperglycaemic action of moxonidine was demonstrated in animal experiments and in clinical studies on patients with differing degrees of hyperglycaemia.

A double-blind study was carried out with a total of 228 patients over a period of 6 weeks.

The patients were randomly divided into 4 groups. All patients each had to take one tablet twice daily. In a preliminary test phase of 4 weeks, all patients received placebo tablets. In the actual test phase one control group (=group K) of patients received placebo tablets, a first test group (=group 1) received tablets containing 0.1 mg of moxonidine per tablet, a second test group (=group 2) received tablets containing 0.2 mg of moxonidine per tablet and a third test group (=group 3) received tablets containing 0.4 mg of moxonidine per tablet. Blood samples were taken from each patient in the fasting state on the day before the start of the test phase and after 6 weeks on the last day of the test phase. The plasma blood sugar values in these were measured in mg of glucose per deciliter.

To assess the results of measurement, a further subdivision into two subgroups each was performed for each of the 4 groups:

A) Subjects having normal starting plasma glucose values in the range of ≦115 mg/dl.

B) Subjects having pathologically elevated starting plasma glucose values of >115 mg/dl. This subgroup includes patients with slightly elevated starting plasma glucose values in the range from 115 to 139 mg/dl and patients with distinctly elevated starting plasma glucose values in the diabetes range (≧140 mg/dl). The results of measurement of these sub-subgroups B1) of diabetes patients were again separately assessed.

The following table indicates for all subgroups the calculated statistical mean values (±standard error) of the plasma blood sugar determinations.

TABLE

Change in plasma glucose values.

| Medication | Patient group | Number of patients | Plasma glucose values in mg/dl (mean values ± standard error) starting value | final value |
|---|---|---|---|---|
| Placebo | K A | 49 | 94 (±1) | 93 (±2) |
| | K B | 9 | 134 (±5) | 129 (±6) |
| | K B 1 | 1 | 172 | 174 |
| 0.1 mg of moxonidine 2 × daily | 1 A | 52 | 95 (±1) | 93 (±2) |
| | 1 B | 7 | 131 (±8) | 117 (±4) |
| | 1 B 1 | 1 | 183 | 103 |
| 0.2 mg of moxonidine 2 × daily | 2 A | 45 | 93 (±2) | 94 (±2) |
| | 2 B | 10 | 170 (±17) | 134 (±8) |
| | 2 B 1 | 6 | 198 (±21) | 144 (±12) |
| 0.4 mg of moxonidine 2 × daily | 3 A | 46 | 92 (±2) | 91 (±2) |
| | 3 B | 10 | 130 (±5) | 120 (±10) |
| | 3 B 1 | 2 | 158 (±7) | 139 (±28) |

From the foregoing table it is evident that during the test phase in all patients treated only with placebo virtually no change in the blood sugar values occurred independently of the starting plasma glucose value. In the patients treated with various doses of moxonidine it was found that in patients with normal starting plasma glucose values likewise virtually no change in the plasma glucose values occurred. In patients with elevated starting plasma glucose values, however, a distinct decrease in these plasma glucose values occurred as a result of the moxonidine treatment, this reduction in the plasma glucose values being greater the higher the starting plasma glucose values.

The foregoing experimental results show that moxonidine exerts an antihyperglycaemic action and causes the reduction of raised blood sugar values without, however, adversely affecting normal blood sugar values. These experimental results are also to be judged as an index for the fact that moxonidine has a favorable effect on insulin resistance. Moxonidine and its acid addition salts are therefore suitable for the treatment of hyperglycaemias.

The doses to be used may vary from individual to individual and of course vary according to the nature of the condition to be treated and the form of administration. In general, daily doses in the range from 0.2 to 0.8 mg, preferably 0.4 to 0.8 mg, are suitable for the treatment of hyperglycaemic conditions in humans by oral administration.

The following example is intended to illustrate in further detail the production of a pharmaceutical preparation containing moxonidine which is suitable for the treatment of hyperglycaemias without, however, restricting the scope of the application.

Example 1: Moxonidine-containing film-coated tablets.

Composition:
Tablet cores:

| | |
|---|---|
| Moxonidine | 0.020 parts |
| Lactose | 9.580 parts |
| Povidone USP | 0.070 parts |
| Crospovidone USP | 0.300 parts |
| Magnesium stearate | 0.030 parts |
| (water | 0.750 parts) |
| Total solid | 10.000 parts |

Film coating:

| | |
|---|---|
| Hydroxypropylmethylcellulose | 0.56 parts |
| 30% aqueous ethylcellulose dispersion | 0.480 parts |
| (Δsolid) | (0.144) parts |
| Polyethylene glycol 6000 | 0.030 parts |
| Titanium dioxide | 0.150 parts |
| Talc | 0.1197 parts |
| Red iron oxide | 0.0003 parts |
| (Water | 3.864 parts) |
| Total solid | 0.600 parts |
| Total amount of film-coating suspension | 4.800 parts |

4.8 kg of the foregoing film-coating suspension were used to coat 10,000 tablet cores each weighing 100 mg.

Tablet Core Production

The moxonidine and the lactose were mixed. The mixture was moistened with a solution of the binder povidone in water and thoroughly kneaded, and the resulting product was spread out on drying racks and dried at a temperature of about 50° C. to a moisture content of at most 0.5%. The dried product was passed through a 0.75 mm screen (Frewitt machine). After mixing the resulting granules with crospovidone and magnesium stearate, tablet cores having a weight of 100 mg were pressed therefrom such that each tablet core contained 0.2 mg of active compound.

Production of the Film-coating Suspension

The hydroxypropylmethylcellulose and the polyethylene glycol 6000 were dissolved in one part of the water. A suspension of talc, titanium dioxide and iron oxide in the remaining water was added to this solution with stirring. The resulting suspension was diluted with the 30% strength aqueous ethylcellulose dispersion with gentle stirring.

Film-coating of the Tablet Cores

The film-coating suspension was sprayed onto the tablet cores in a film-coating apparatus, while warm air at about 70° C. warmed the tablet cores to a temperature of about 45° C. The film-coated tablets were then dried for 16 hours at a temperature of about 45° C.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method of treating a mammal having an elevated blood glucose level resulting from increased glucose release or decreased metabolic glucose utilization connected with at least one glucose metabolism affecting condition selected from the group consisting of insulin resistance, glucose intolerance, type II diabetes and obesity, said method comprising lowering the blood glucose level of said mammal toward a normal value by administering to said mammal an effective elevated blood glucose level lowering amount of 4-chloro-5-{(4,5-dihydro-1H-imidazol-2-yl)amino}-6-methoxy-2-methylpyrimidine of formula I

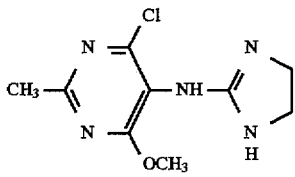

or a physiologically acceptable acid addition salt thereof.

2. A method according to claim 1, wherein said 4-chloro-5-(4,5-dihydro-1H-imidazol-2-yl)amino-6-methoxy-2-methylpyrimidine or salt thereof is incorporated into a dosage form selected from the group consisting of uncoated tablets, coated tablets, capsules, powders, granules, solutions, suspensions and emulsions and is administered orally.

3. A method according to claim 1, wherein said mammal having an elevated blood glucose level has a starting plasma glucose level of >115 mg/dl.

4. A method of inhibiting hyperglycemia resulting from increased glucose release or decreased metabolic glucose utilization connected with at least one glucose metabolism affecting condition selected from the group consisting of insulin resistance, glucose intolerance, type II diabetes and obesity, said method comprising administering to said mammal an effective hyperglycemia inhibiting amount of 4-chloro-5-{(4,5-dihydro-1H- imidazol -2-yl) amino}-6-methoxy-2-methylpyrimidine of formula I

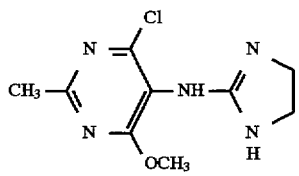

or a physiologically acceptable acid addition salt thereof in the absence of other anti-hyperglycemic agents.

5. A method according to claim 4, wherein said 4-chloro-5-(4,5-dihydro-1H-imidazol-2-yl)amino-6-methoxy-2-methylpyrimidine or salt thereof is incorporated into a dosage form selected from the group consisting of uncoated tablets, coated tablets, capsules, powders, granules, solutions, suspensions and emulsions and is administered orally.

6. A method of treating a mammal in need of anti-hyperglycemic treatment due to at least one glucose metabolism affecting condition selected from the group consisting of insulin resistance, glucose intolerance, type II diabetes and obesity, said method comprising counteracting elevated blood glucose levels by administering to said mammal an effective elevated blood glucose level lowering amount of 4-chloro-5-{(4,5-dihydro-1H-imidazol-2-yl)amino}-6-methoxy-2-methylpyrimidine of formula I

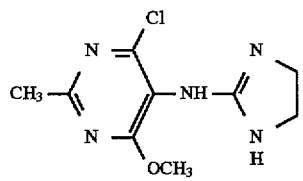

or a physiologically acceptable acid addition salt thereof.

7. A method according to claim 6, wherein said 4-chloro-5-(4,5-dihydro-1H-imidazol-2-yl)amino-6-methoxy-2-methylpyrimidine or salt thereof is incorporated into a dosage form selected from the group consisting of uncoated tablets, coated tablets, capsules, powders, granules, solutions, suspensions and emulsions and is administered orally.

8. A method according to claim 7, wherein said 4-chloro-5-(4,5-dihydro-1H-imidazol-2-yl)amino-6-methoxy-2-methylpyrimidine or salt thereof is administered at a dosage of from 0.2 to 0.8 mg per day.

9. A method according to claim 8, wherein said or salt thereof is administered at a dosage of from 0.4 to 0.8 mg per day.

10. A method according to claim 6, wherein said mammal in need of anti-hyperglycemic treatment has a starting plasma glucose level of >115 mg/dl.

11. A method according to claim 6, wherein said mammal in need of anti-hyperglycemic treatment has a starting plasma glucose level of $\geq 140$ mg/dl.

12. A method according to claim 6, wherein said mammal having an elevated blood glucose level has a starting plasma glucose level of $\geq 140$ mg/dl.

* * * * *